United States Patent [19]
Demopulos et al.

[11] Patent Number: 6,106,556
[45] Date of Patent: Aug. 22, 2000

[54] TENDON AND LIGAMENT REPAIR SYSTEM

[75] Inventors: Gregory A. Demopulos, Mercer Island, Wash.; Stephen A. Yencho, Menlo Park, Calif.; David A. Herrin, Seattle, Wash.; Neil G. McIlvaine, Seattle, Wash.; Michael D. Nelson, Seattle, Wash.; Milton R. Sigelmann, Seattle, Wash.; Jose T.V. de Castro, Newton, Mass.; George Selecman, Marblehead, Mass.; John Collins, N. Turramurra, Australia; Imrann Aziz, Stanford, Calif.; Gorm Bressner, Providence, R.I.; Nicholas R. Kalayjian; Charles S. McCall, both of San Francisco, Calif.; Robert W. Mericle, Eden, N.C.

[73] Assignee: Omeros Medical Systems, Inc., Seattle, Wash.

[*] Notice: This patent is subject to a terminal disclaimer.

[21] Appl. No.: 09/182,759

[22] Filed: Oct. 29, 1998

Related U.S. Application Data

[63] Continuation-in-part of application No. 09/086,126, May 28, 1998, which is a continuation of application No. 08/567,311, Dec. 4, 1995, Pat. No. 5,800,544, which is a continuation-in-part of application No. 08/349,358, Dec. 2, 1994, abandoned.

[51] Int. Cl.[7] .................................................. A61F 2/08
[52] U.S. Cl. ............................... 623/13.16; 623/13.18; 606/72; 606/59
[58] Field of Search ............................ 623/11, 13, 13.15, 623/13.16, 13.18, 13.13, 13.14, 13.12, 13.11, 11.11; 606/53, 72, 59, 71

[56] References Cited

U.S. PATENT DOCUMENTS 3,124,136 3/1964 Usher .
3,176,316 4/1965 Bodell .

(List continued on next page.)

FOREIGN PATENT DOCUMENTS

WO 96/16612 6/1996 WIPO .

OTHER PUBLICATIONS

Boynton, M.D. and Fadale, P.D., The basic science of anterior cruciate ligament surgery. *Orthop. Rev.* 22:673–679 (1993).

Hoffmann, M.W. et al., Repair and reconstruction of the anterior cruciate ligament by the "sandwich technique", *Arch. Orthop. Trauma Surg.*, 112:113–120 (1993).

Lazovic, D. and Messner, K., Collagen repair not improved by fibrin adhesive, *Acta Orthop. Scand.*, 64:583–586 (1993).

Lyon, R.M. et al., Ultrastructural differences between the cells of the medial collateral and the anterior cruciate ligaments, *Clin. Orthop.*, 279–286 (1991).

Nogalski, M.P. and Bach, B.R., Jr., A review of early anterior cruciate ligament surgical repair or reconstruction, *Orthop., Rev.* 2:2:1213–1223 (1993).

Paessler, H.H., et al., Augmented repair and early mobilization of acute anterior cruciate ligament injuries, *Am. J. Sports Med.*, 20:667–674 (1992).

Sgaglione, N.A., et al., Primary repair with semitendinosus tendon augmentation of acute anterior cruciate ligament injuries, *Am. J. Sports Med.*, 18:64–73 (1990).

(List continued on next page.)

*Primary Examiner*—Paul B. Prebilic
*Attorney, Agent, or Firm*—Christensen O'Connor Johnson & Kindness PLLC

[57] ABSTRACT

A rigid or semi-rigid reinforcement member is inserted into or over the damaged portion of an injured tendon or ligament. The tendon or ligament is connected to the reinforcement member such that the cord-member combination can immediately withstand normal tensile forces. The interconnection can be mechanical, such as by pins extending through the sleeve reinforcement member and cord. The sleeve can be bioabsorbable over a sufficiently long period of time that the cord is healed by the time the sleeve is absorbed.

23 Claims, 12 Drawing Sheets

U.S. PATENT DOCUMENTS

| | | | |
|---|---|---|---|
| 3,545,008 | 12/1970 | Bader, Jr. . | |
| 3,646,615 | 3/1972 | Ness . | |
| 3,805,300 | 4/1974 | Tascon-Alonso et al. . | |
| 3,833,002 | 9/1974 | Palma . | |
| 3,842,441 | 10/1974 | Kaiser . | |
| 3,987,497 | 10/1976 | Stoy et al. . | |
| 3,992,725 | 11/1976 | Homsy . | |
| 4,246,660 | 1/1981 | Wevers . | |
| 4,414,967 | 11/1983 | Shapiro . | |
| 4,469,101 | 9/1984 | Coleman et al. . | |
| 4,501,029 | 2/1985 | McMinn . | |
| 4,512,038 | 4/1985 | Alexander et al. . | |
| 4,534,349 | 8/1985 | Barrows . | |
| 4,535,763 | 8/1985 | Jaquet . | |
| 4,610,688 | 9/1986 | Silvestrini et al. . | |
| 4,643,734 | 2/1987 | Lin . | |
| 4,755,183 | 7/1988 | Kenna . | |
| 4,776,851 | 10/1988 | Bruchman et al. . | |
| 4,828,562 | 5/1989 | Kenna | 623/13 |
| 4,870,957 | 10/1989 | Goble et al. . | |
| 4,950,271 | 8/1990 | Lewis et al. . | |
| 4,960,420 | 10/1990 | Goble et al. | 606/72 |
| 4,979,956 | 12/1990 | Silvestrini . | |
| 4,997,433 | 3/1991 | Goble et al. | 606/64 |
| 5,002,574 | 3/1991 | May et al. . | |
| 5,011,486 | 4/1991 | Aebischer et al. . | |
| 5,061,281 | 10/1991 | Mares et al. . | |
| 5,061,283 | 10/1991 | Silvestrini . | |
| 5,108,433 | 4/1992 | May et al. . | |
| 5,122,151 | 6/1992 | de Medinaceli . | |
| 5,147,362 | 9/1992 | Goble . | |
| 5,151,104 | 9/1992 | Kenna . | |
| 5,250,055 | 10/1993 | Moore et al. . | |
| 5,306,301 | 4/1994 | Graf et al. . | |
| 5,314,427 | 5/1994 | Goble et al. | 606/72 |
| 5,374,269 | 12/1994 | Rosenberg . | |
| 5,425,766 | 6/1995 | Bowald . | |
| 5,458,601 | 10/1995 | Young, Jr. et al. . | |
| 5,458,636 | 10/1995 | Brancato . | |
| 5,690,631 | 11/1997 | Duncan et al. | 606/71 |
| 5,722,976 | 3/1998 | Brown | 606/71 |
| 5,723,008 | 3/1998 | Gordon . | |
| 5,800,544 | 9/1998 | Demopulos et al. | 623/13 |

OTHER PUBLICATIONS

Sherman, M.F., et al., The long–term followup of primary anterior cruciate ligament repair: Defining a rationale for augmentation, *Am. J. Sports Med.*, 19:243–255 (1991).

Wiig, M.E., et al., The early effect of high molecular weight hyaluronan (hyaluronic acid) on anterior cruciate ligament healing: An experimental study in rabbits, *J. Orthop. Res.*, 8:425–434 (1990).

Flexor tendon repair: Indiana Method, *The Indiana Hand Center Newsletter*, 1:1–20 (1993).

Ketchum, L.D. Primary tendon healing: A review, *J. Hand Surg.*, 2(6):428–435 (1977).

Richards, H.J., Repair and healing of the divided digital flexor tendon, *The Brithsh Journal of Accident Surgery*, 12:1–12.

Furlow, L.T., Jr., The role of tendon tissues in tendon healing, 57:39–49 (1976).

Gelberman, R.H., et al., Influences of flexor sheath continuity and early motion on tendon healing in dogs, *J. Hand Surg.*, 15A:69–77 (1990).

Gelberman, R.H., et al., Fibroblast chemotaxis after tendon repair, *J. Hand Surg.*, 16A:686–693 (1991).

Gelberman, R.H., et al., The revascularization of healing flexor tendons in the digital sheath, *J. Bone and Joint Surg., Inc.*, 73A:868–881 (1991).

Becker, H., Primary repair of flexor tendons in the hand without immobilization—Preliminary report, *The Hand* 10:37–47 (1978).

Goodship, A.E., et al., The development of tissue around various prosthetic implants used as replacements for ligaments and tendons, *Clin. Ortho. and Related Res.*, 196:61–68 (1985).

Engebretsen, L., et al., A prospective, randomized study of three surgical techniques for treatment of acute ruptures of the anterior cruciate ligament, *Am. J. Sports Med.*, 18:585–590 (1990).

Kennedy, J.C., et al., Presidential address: Intraarticular replacement in the anterior cruciate ligament–deficient knee, *Am. J. Sports Med.*, 8:1, 7–8 (1980).

Strover, A.E., and Firer, P., The use of carbon fiber implants in anterior cruciate ligament surgery, *Clin. Ortho. and Related Res.*, 196:88–89 (1985).

Cross, M.J., et al., Acute repair of injury to the anterior cruciate ligament. A long–term followup, *Am. J. Sports Med.*, 21:128–131 (1993).

Manske, P.R., The flexor tendon, *Orthopedics*, 10:1733–1741 (1987).

Pring, D.J., et al., The mechanical properties of human flexor tendons in relation to artificial tendons, *J. Hand Surg.*, 10B:331–336 (1985).

Doyle, J.R., Anatomy of the finger flexor tendon sheath and pulley system, *J. Hand Surg.*, 13A:473–484 (1988).

Strum, G.M. and Larson, R.L., Clinical experience and early results of carbon fiber augmentation of anterior cruciate reconstruction of the knee, *Corr.*, 196:124–138 (1985).

Park, J.P., et al., A high–strength dacron augmentation for cruciate ligament reconstruction, *Corr.*, 196:175–185 (1985).

McPherson, G.K., et al., Experimental mechanical and histologic evaluation of the Kennedy ligament augmentation device, *Corr.*, 196:186–195 (1985).

Bolton, C.W. and Bruchman, W.C., The GORE–TEX™ expanded polytetrafluoroethylene prosthetic ligament: An in vitro and in vivo evaluation, *Corr.*, 196:202–213 (1985).

Silfverskild, K.L., et al., Two new methods of tendon repair: An in vitr evaluation of tensile strength and gap formation, *J. Hand Surg.*, 18A:58–65 (1993).

Dodds, J.A., et al., Anatomy of the anterior cruciate ligament: A blueprint for repiar and reconstruction, *J. Arthroscopic and Related Surgery*, 10(2):132–139 (1994).

Radford, W.J.P., et al., Immediate Strength After Suture Of A Torn Anterior Cruciate Ligament, *J. of Bone and Joint Surgery*, 76–B:480–483 (1994).

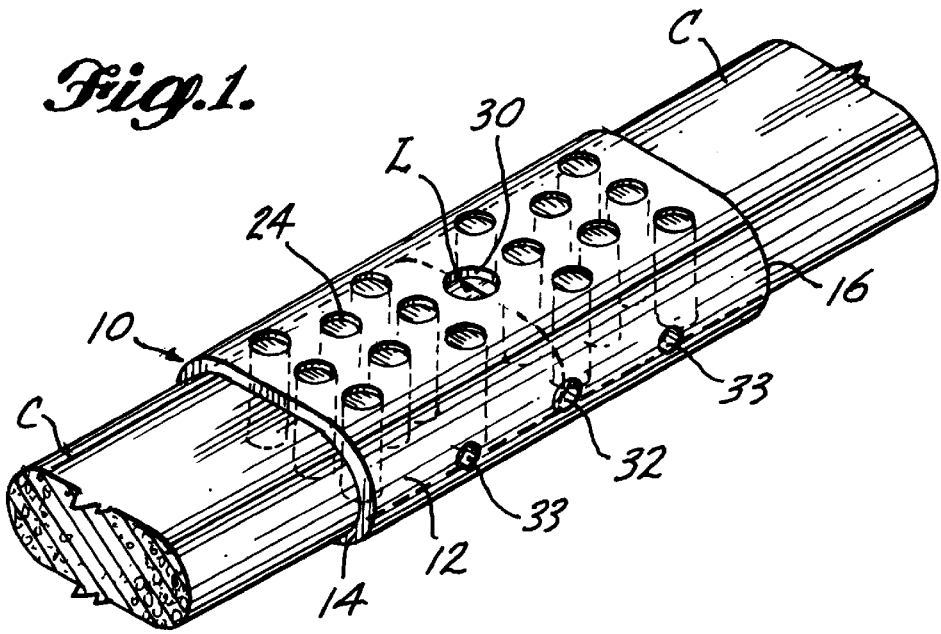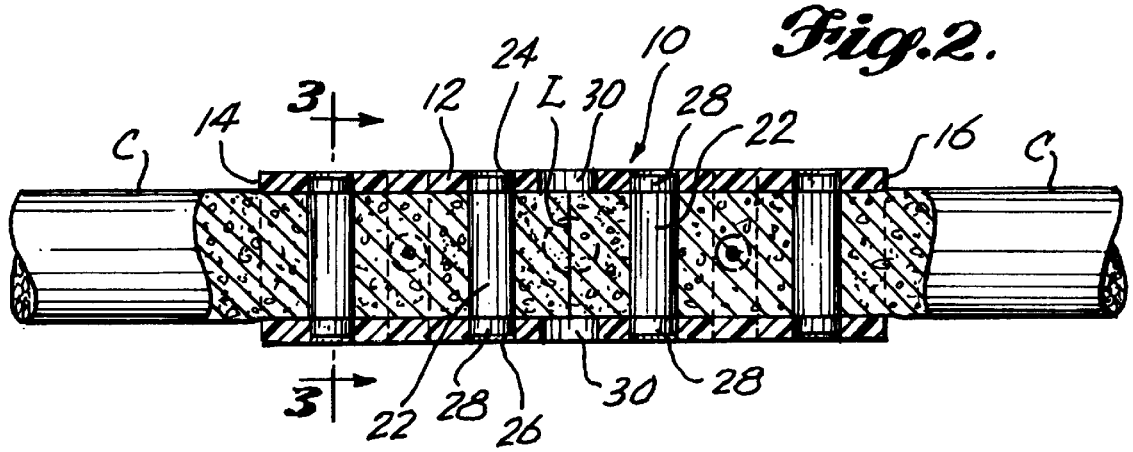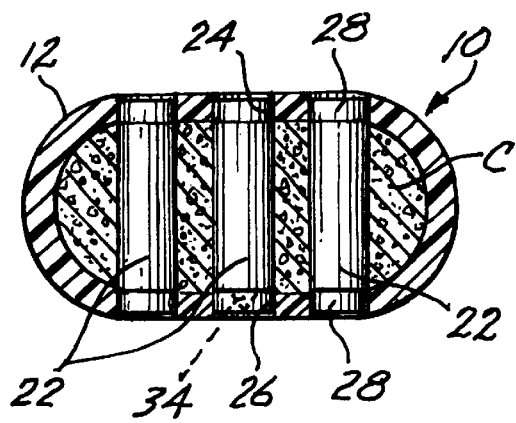

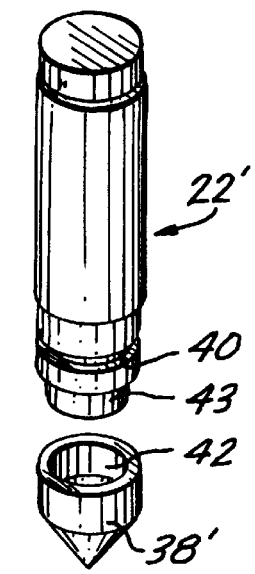
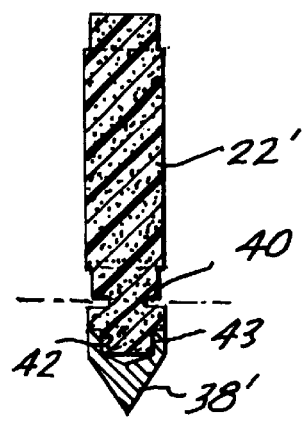
Fig. 7.  Fig. 8.
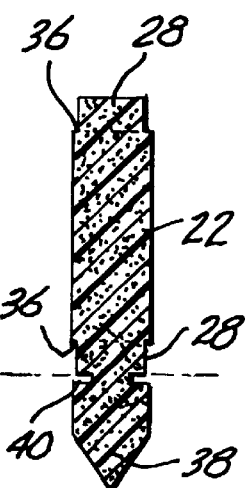
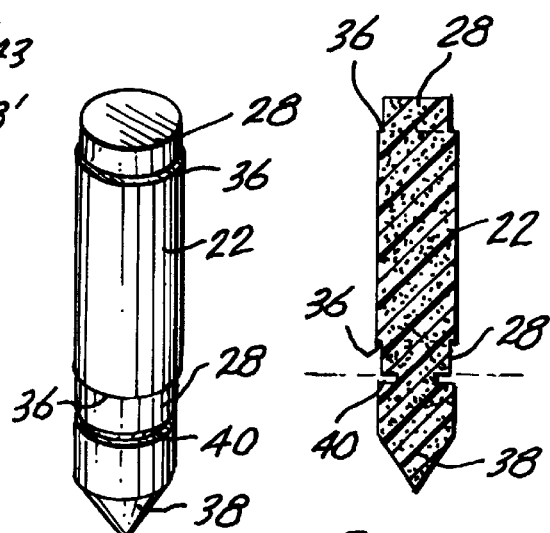
Fig. 5.  Fig. 6.
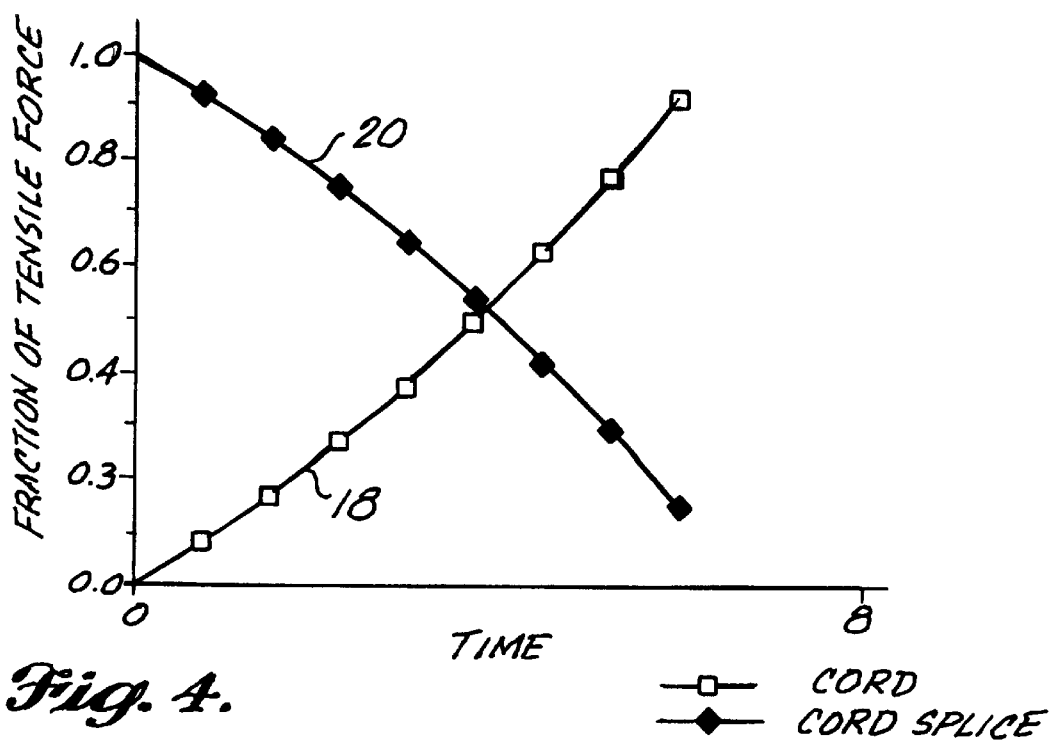
Fig. 4.

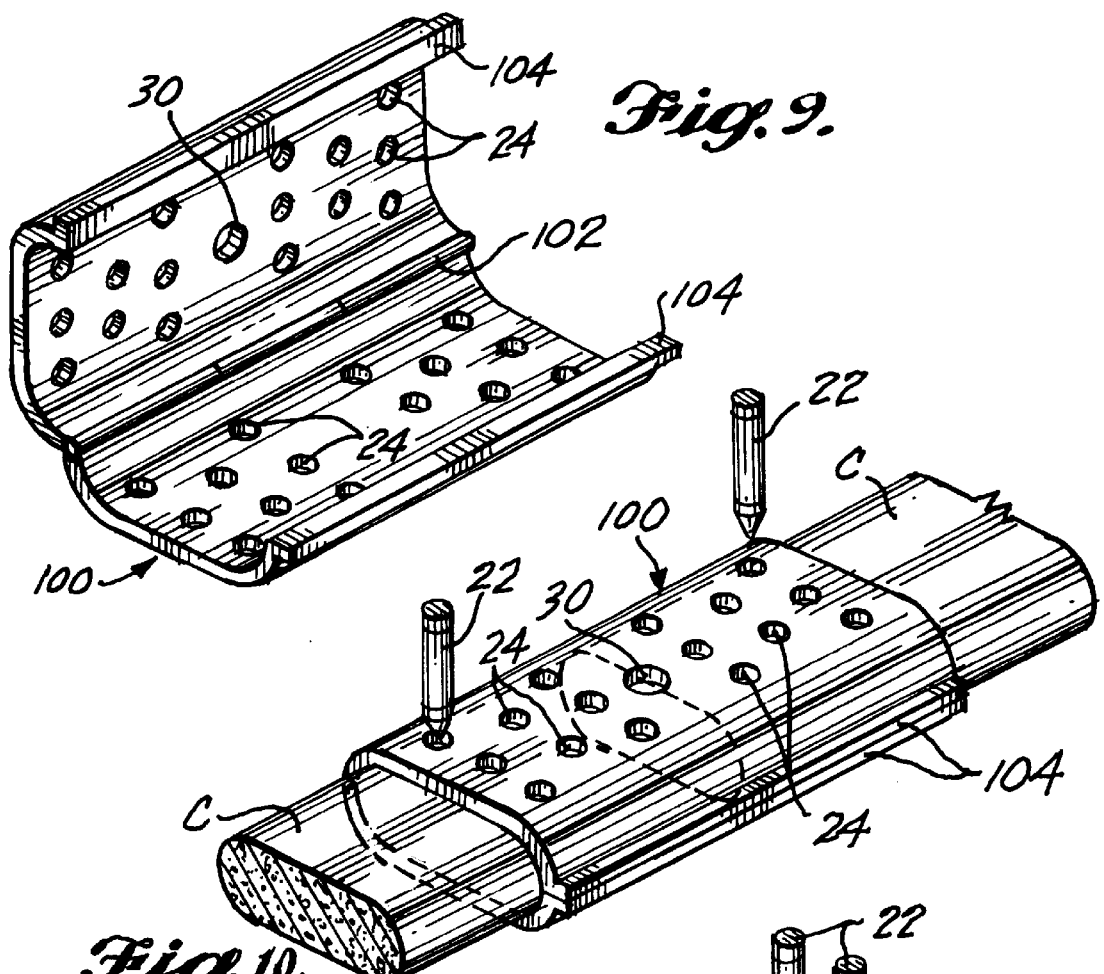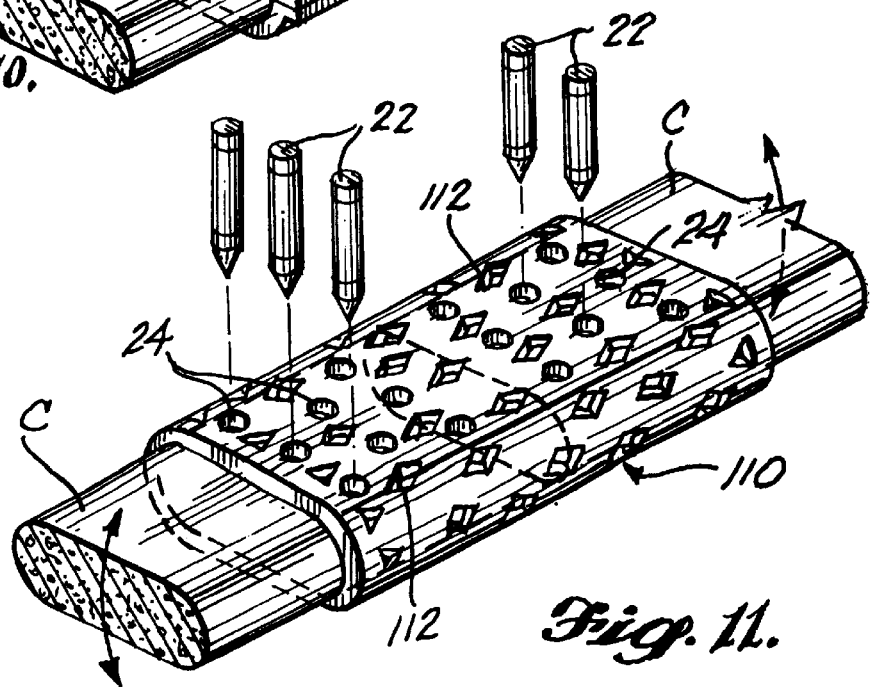

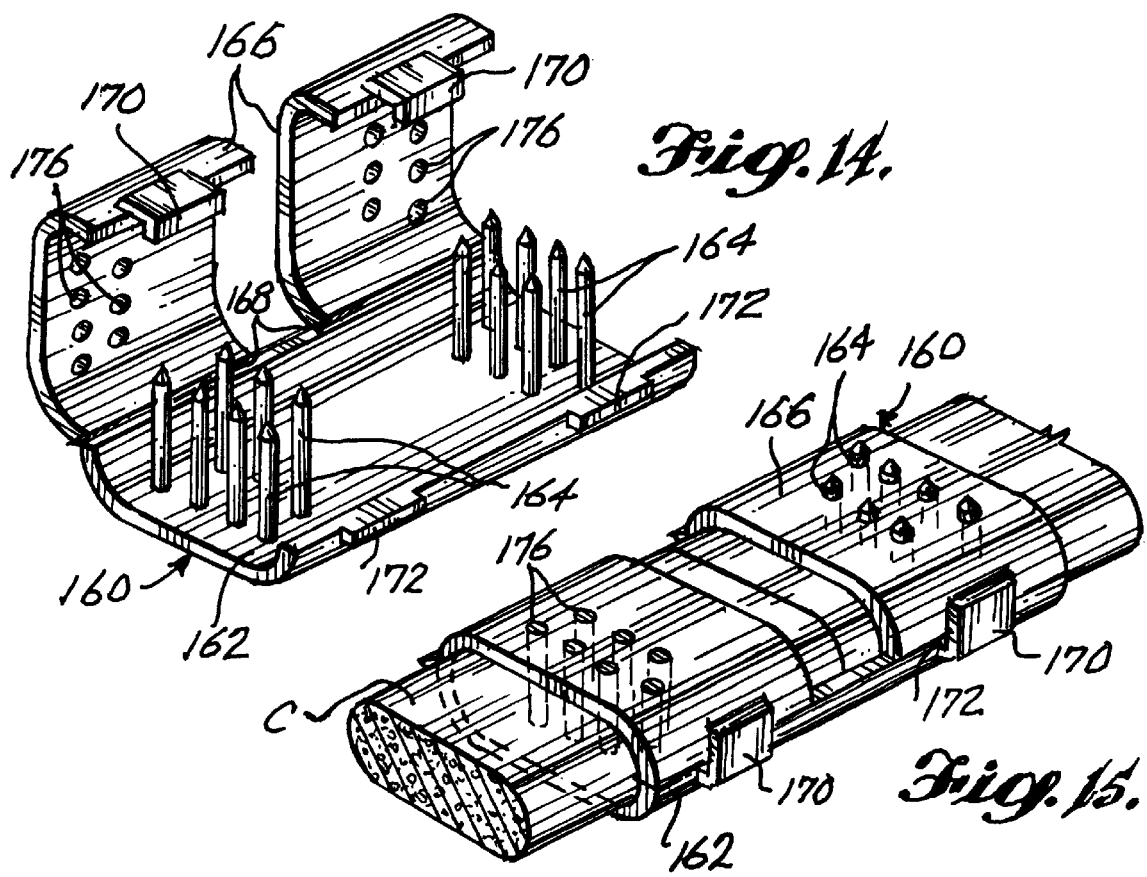

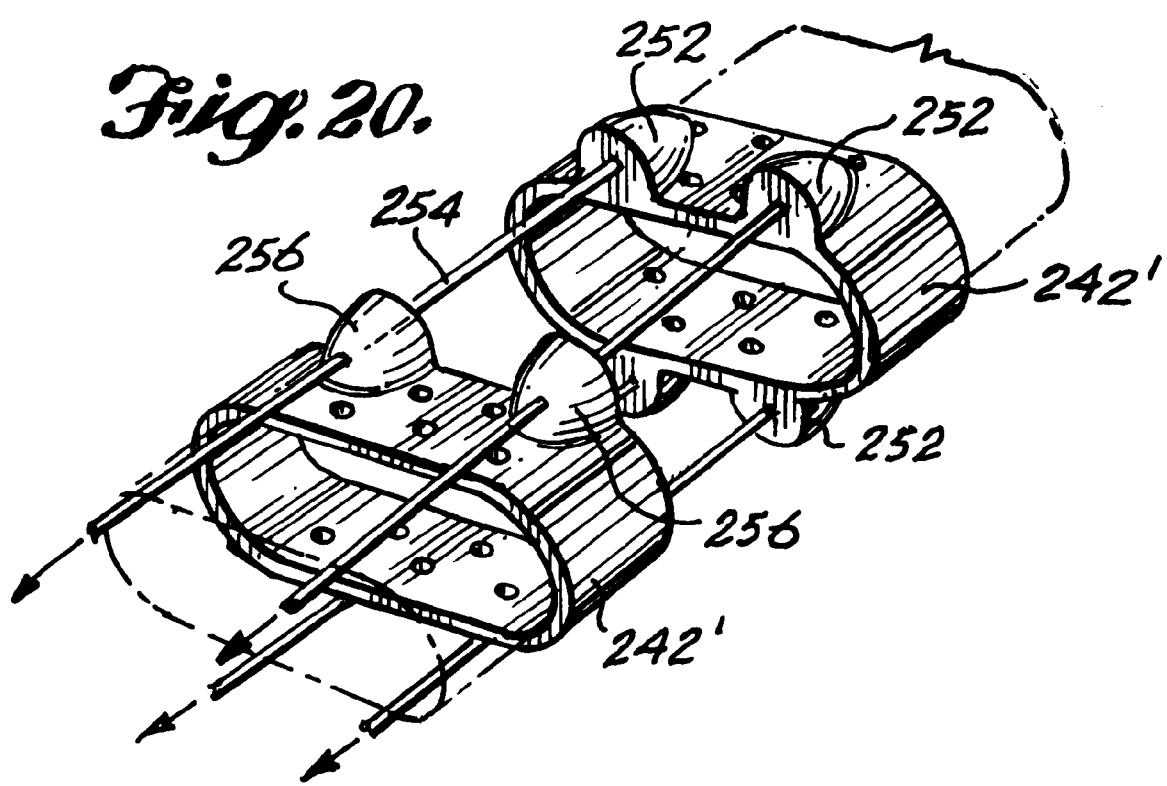

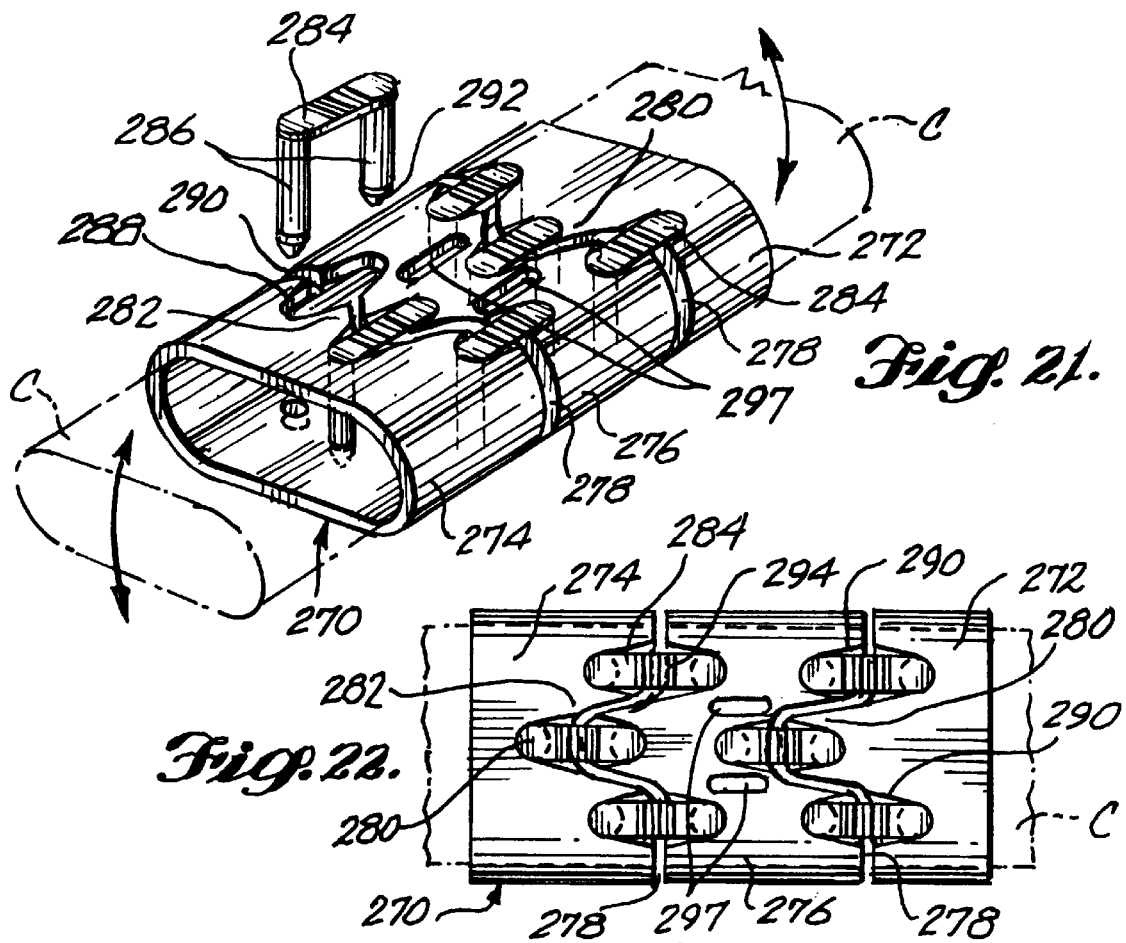

TENDON AND LIGAMENT REPAIR SYSTEM

This application is a continuation-in-part of U.S. patent application Ser. No. 09/086,126, filed on May 28, 1998, titled "TENDON AND LIGAMENT REPAIR SYSTEM," which is a continuation of U.S. patent application Ser. No.08/567,311, filed on Dec. 4, 1995, titled "TENDON AND LIGAMENT REPAIR SYSTEM," now U.S. Pat. No. 5,800,544, which is a continuation-in-part of U.S. patent application Ser. No. 08/349,358, filed on Dec. 2, 1994, titled "TENDON AND LIGAMENT SPLICE," now abandoned, all of which are expressly incorporated by reference herein; and this application claims the benefit of U.S. Provisional Application No. 60/063,892, filed on Oct. 29, 1997.

FIELD OF THE INVENTION

The present invention relates to a system for repairing lacerated or severed fibrous connective tissue, referred to herein as "connective cords" or "cords," particularly tendons and ligaments.

BACKGROUND OF THE INVENTION

Repair techniques for lacerated or severed tendons and ligaments ("connective cords" or "cords") vary widely depending on the nature of the injury and the particular cord affected. There are large differences in the extent to which access can be obtained in the least obtrusive manner, in the amount of cord excursion, in the surrounding environment, in the stresses to which different cords are normally subjected, and in the healing characteristics of different cords. In addition, often there is no consensus of the overall best way to repair a given cord. Examples of often injured cords having different accepted repair techniques are flexor tendons of the hand and the anterior cruciate ligament (ACL) of the knee.

For example, repair of a long flexor tendon that has been severed is typically achieved by suturing the severed tendon ends face-to-face. Historically, the joints across which the tendon acts were immobilized for from three to eight weeks to protect the tendon while it healed, because a freshly sutured tendon can withstand only a fraction of the tensile force to which a healthy tendon is subjected during normal use. Immobilization results in scarring and adhesion formation along the length of the tendon. Range of motion is adversely affected, particularly in the case of flexor tendons which normally glide smoothly through and over the unique system of tendon tunnels and pulleys of the hand. Nevertheless, it was thought that fibroblastic ingrowth was required in order for the tendon to heal, such that immobilization and the resulting decreased range of motion were considered necessary evils in order for effective healing to take place. More recently it has been discovered that flexor tendons have an intrinsic capacity to heal and that limited motion will actually expedite healing. Still, exercises must be carefully planned and carried out due to the weakness of the sutured repair. In early stages of healing, protected passive and/or restricted active exercises may be used, followed by tendon gliding and active strengthening exercises in later stages. The affected joints are most often partially immobilized to prevent inadvertent application of excess force.

In the case of an anterior cruciate ligament (connecting the bottom of the femur and the top of the tibia) the stresses resulting from applied forces are much greater, there is less interaction with surrounding tissue and bone, the excursion of the cord is less, and the healing tendencies are vastly different. Despite numerous studies, there still is no universally accepted repair procedure, and prevailing procedures are difficult and intricate. The current "standard of care" remains the reconstruction of the ACL using a bone-tendon-bone or tendon autograft (i.e., harvested from the patient). However, there are multiple problems with autografting: (1) the intact ACL possesses important mechanoreceptive and proprioceptive capabilities, and graft reconstruction sacrifices these capabilities; (2) autografting involves considerable donor site morbidity; (3) to avoid donor site morbidity, occasionally a cadaveric graft is used, which carries the risk of disease transmission.

These problems with ACL reconstruction have led to renewed interest in primary repair of the ACL. In the case of primary repair without augmentation, small bores are drilled in the adjacent bones approximately at the anatomically correct sites for normal connection of the ACL. Multiple loops of suture are used for reconnecting the ligamentous stumps to the bone. Several loops of permanent suture can provide an initial strong repair. However, over time the strength of the repaired ACL often decreases, which is indicative of a failure in the healing process. In general, it is now accepted that healing tendencies of the intra-articular ACL are poor, particularly when compared to the neighboring extra-articular medial collateral ligament which heals readily.

Failure or long-term weakening of ACL primary repair has led to techniques for "augmenting" a primary repair. These can involve suturing biological material, such as a section of patellar tendon, across a repair site, and the use of artificial augmenting strips or sheaths which typically have been flexible and fibrous in the hope that healing of the ACL will be promoted, rather than being inhibited by, the close proximity of an artificial "shield." Strips or bands of Dacron, polyethylene or carbon fiber have had their opposite ends stapled or otherwise anchored to the adjacent bones to provide the primary or secondary support for the "healing" ACL.

SUMMARY OF THE INVENTION

The present invention provides a system for repair of injured connective cords by application of a reinforcing member of substantially rigid or semi-rigid material, such member being adapted for extending longitudinally between severed end portions of a connective cord with the severed end portions in abutting relationship, and securing the cord to the reinforcing member such that tension applied to the cord is transmitted through the reinforcing member. The reinforcing member and mechanism securing it to the cord maintain the severed cord ends abutting as tension is applied to the cord by transmitting tensional force through the reinforcing member. In one aspect of the present invention, the severed ends of the cord are secured to the reinforcing member by a plurality of pins anchored in the reinforcing member and extending at least part way through the connective cord for transmission of tensional force from the connective cord through the pins and the reinforcing member. The reinforcing member can extend internally or externally of the cord. For example, the affected cord ends can be enclosed in a hollow reinforcing sleeve and the adjacent end portions of the cord secured inside the sleeve. In other embodiments, the reinforcing member can be inserted internally of the adjacent cord end portions, and such end portions secured to the internal reinforcing member. Connection pins can be arranged in rows with pins of adjacent rows staggered and with adjacent pins spaced apart sufficiently to prevent inordinate localized stresses from being applied to the tissue when the tendon is tensioned.

In the case of a tendon that normally glides along adjacent tissue and/or bone, it is important that the reinforcing member and mechanical connection components not interfere with the gliding motion. The mechanical interconnection of the cord ends and the reinforcing member preferably is sufficiently strong that immobilization is not required. Strengthening and healing promoting exercises can begin almost immediately.

The reinforcing member and any mechanical connection components can be bioabsorbable. The period of bioabsorbability is selected based on the healing characteristics of the affected connective cord. Ideally, the reinforcing member and mechanical connection components will remain sufficiently strong over time such that the overall force that the repaired connective cord can withstand always is at least as great as the force to which it is normally subjected. For example, in the early stages when the cord itself has essentially no resistance to separation, the reinforcing member and connection components will withstand a strong tensile force. As the connective cord heals and is capable of withstanding substantial force on its own, the partially absorbed reinforcing member and connection components need not withstand as much force as at the outset.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a top perspective of a severed fibrous cord of connective tissue repaired in accordance with one aspect of the system of the present invention;

FIG. 2 is a side elevation of the repaired cord of FIG. 1, with parts broken away;

FIG. 3 is a vertical transverse section along line 3—3 of FIG. 2;

FIG. 4 is a graph illustrating the relative strengths of a splice in accordance with the present invention and a healing connective cord over time;

FIG. 5 is a top perspective of a component of the splice in accordance with the present invention, namely, a connection pin, and FIG. 6 is a longitudinal section thereof;

FIG. 7 is a top perspective of an alternative connection pin, with parts shown in exploded relationship, and FIG. 8 is a longitudinal section thereof with parts assembled;

FIG. 9 is a top perspective of an alternative splice in accordance with the present invention, and FIG. 10 is a corresponding top perspective of the splice of FIG. 9 with parts in different positions;

FIG. 11 is a top perspective of another embodiment of a splice in accordance with the present invention;

FIG. 14 is a top perspective of an alternative splice in accordance with the present invention, and FIG. 15 is a top perspective of the splice of FIG. 14 with parts in different positions;

FIG. 20 is a top perspective of another form of a splice in accordance with the present invention with parts partially assembled;

FIG. 21 is a top perspective of another embodiment of a splice in accordance with the present invention, with some parts shown in exploded relationship, and FIG. 22 is a fragmentary enlarged top plan of a portion of the splice of FIG. 21;

FIG. 23 is a top perspective of another embodiment of a splice in accordance with the present invention, and FIG. 24 is a fragmentary side elevation of a portion thereof;

DETAILED DESCRIPTION OF THE PREFERRED EMBODIMENT

Figure 13:
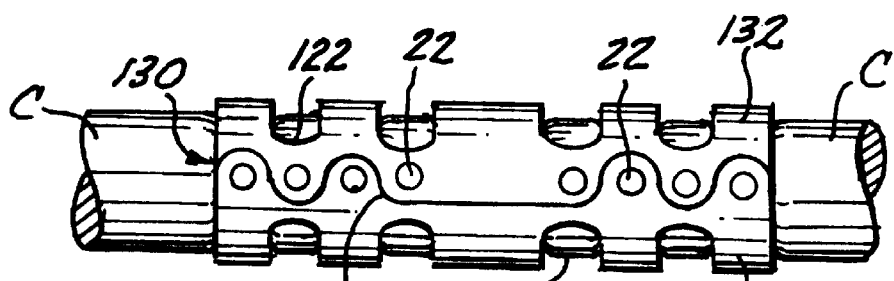
FIG. 13 is a side elevation of the splice of FIG. 12.

The present invention is used for repairing lacerated or severed fibrous connective tissue ("connective cords"), particularly ligaments and tendons. One embodiment of a splice 10 in accordance with the invention is illustrated in FIGS. 1, 2 and 3 in conjunction with a connective cord C, such as a flexor tendon, separated at a location L intermediate its opposite end connections (not shown) to adjacent bone and muscle. Relative sizes of the cord and splice components are exaggerated in the drawings for ease of illustration and description.

The primary component of the splice 10 is a unitary, substantially rigid or semi-rigid reinforcement member, in this case a sleeve 12. The interior of the sleeve is of substantially uniform cross section from one end 14 to the other end 16, sized to snugly receive the severed end portions of the cord. The separation location L is situated midway between the sleeve ends. In accordance with the present invention, the cord end portions are secured within the sleeve so as to maintain the separated ends in abutting relationship to promote healing. In addition, the severed end portions are interconnected with the sleeve for substantially uniform distribution of force across the cord. Tension can be applied to the cord through the splice even before any healing has occurred, thereby enabling normal functioning of the repaired cord immediately or soon after the repair. Thus, in characterizing the sleeve as preferably being "rigid or semi-rigid", one important characteristic is that the dimensions and general shape of the sleeve not change substantially as normal tension is applied to a cord secured in the sleeve, it being particularly important that force applied to the cord be transmitted through the sleeve. In the case of a severed cord, it is desirable for the severed ends of the cord to abut within the sleeve and maintain the abutting relationship despite tension being applied to the cord. Further, as described in more detail below, in the case of mechanical fasteners for securing a cord within the sleeve, preferably the rigid or semi-rigid character of the sleeve results in the fasteners being stably positioned without substantial deflection caused by tension applied to the cord.

For many connective cords, including flexor tendons, severed cord ends maintained in abutting relationship will heal over time and gradually regain the pre-injury strength. In accordance with the present invention, the splice 10 can be formed of a rigid or semi-rigid bioabsorbable polymer. The ideal relationship of the strength of the splice as compared to the strength of the healing cord is illustrated in FIG. 4. As represented by line 18, initially (time "0") the abutting severed cord ends will not inherently withstand tension whereas, as represented by line 20, at t=0 the splice and cord connection will withstand the entire maximum force to which the cord would be subjected in normal use. The splice weakens as it is absorbed into the body, as indicated by the downward slope of line 20. At the same time, the repair site heals and strengthens. Ideally, at each stage of healing the combined strength of the splice and the healing cord is at least equal to the maximum force to which the cord is normally subjected. In the case of a flexor tendon, normal healing is completed by about twelve weeks, at which time the tendon itself usually will withstand normal forces and the splice is no longer required. An appropriate blend of bioabsorbing polymer, such as polydioxanone (PDO), polyglycolic acid (PGA), polylactic acid (PLA) or a PGA/PLA copolymer, can be selected based on the healing characteristics of the particular connective cord repaired and the dimensional requirements for the splice in order to achieve the desired strength and bioabsorbing properties. In addition, the sleeve and/or the components securing it to the cord can be coated or impregnated with an agent or agents to enhance healing or decrease adhesion or scar formation such as hyaluronic acid, angiogenic factors, growth factors and/or collagenase inhibitors. Such agents can immediately diffuse into the body directly adjacent to the repair, and/or be released over time as the sleeve is absorbed.

In the case of connective cords that move along or through adjacent tissue, bone, etc., and particularly in the case of flexor tendons which pass through a series of fibro-osseous tunnels and pulleys of the hand, the cross-sectional shape of the sleeve 12 should approximate the shape of the connective cord when moving under tension. In the case of a flexor tendon, the cord is oval when under tension and, accordingly, the shell 12 is of oval cross section. In a representative application repairing a flexor tendon, the shell can have an inside upright minor axis dimension of about 0.094 inch and an inside horizontal major axis dimension at least about twice the length of the minor axis. The length of the splice shell must be large enough to allow securing of a sufficient segment of each severed end portion without application of localized forces that could further tear, lacerate or otherwise injure the cord ends. The sleeve also can be short enough to allow for bending of the flexor tendon through the pulley system of the hand. In a representative embodiment as used for repairing a flexor tendon, the length of the sleeve 12 can be about 0.340 inch, substantially greater than the maximum cross-sectional dimension. For smooth gliding, the shell wall should be as thin as possible, about 0.025 inch to 0.029 inch in a representative embodiment, and certainly much less than one-half the minor axis of the sleeve. The ends of the sleeve can be chamfered to ease sliding of the sleeve.

In the embodiment illustrated in FIGS. 1, 2 and 3, the severed end portions of the cord C are interconnected with the sleeve by pins 22 extending between the top and bottom walls of the sleeve. Several pins are provided at each side of the separation location L, preferably arranged in transversely extending rows. To prevent application of localized forces when the cord is under tension, pins of each row at each side of the separation location are staggered relative to the pins of an adjacent row. Also, it is preferred that the pins be of small diameter, approximately 0.023 inch to 0.032 inch in the representative embodiment, and at each side of the separation location the pins should be spaced apart a distance at least as great as the pin diameter. In the illustrated embodiment, the pins are provided in a 3-2-3 staggered configuration at each side.

Each pin 22 extends through aligned holes 24 and 26 in the top and bottom sleeve walls, respectively. As described below, the pins 22 can be driven through the aligned holes. Preferably, each pin has opposite end portions 28 of slightly reduced diameter as compared to the central portion of the pin extending through the tendon, such that narrow shoulders of the pins abut against the inner periphery of the shell to maintain the pins in position. The outer ends of the pins preferably are substantially flush with the outer periphery of the sleeve so that they will not snag or irritate adjacent tissue.

The top and bottom walls of the sleeve have aligned observation ports 30 large enough that the cord ends may be viewed so that the separation location L can be precisely positioned at the center of the sleeve. In the representative embodiment, the observation ports can be about 0.050 inch in diameter. At the sides, additional central observation ports 32 are provided, as well as smaller ports 33 toward the ends for the purpose of permitting synovial fluid to diffuse into and through the shell to promote healing. Similarly, as seen in FIG. 3, the inner periphery of the shell can be provided with one or more V grooves 34 to allow blood flow to the cord. The sizes of ports 33 and groove 34 are not critical, except that care must be taken that the additional ports and groove(s) do not unduly weaken the sleeve.

With reference to FIG. 5 and FIG. 6, each pin 22 can be molded of a suitable polymer with the reduced diameter end portions 28 forming the narrow, outward facing annular shoulders 36 for engaging against the inner periphery of the sleeve adjacent to the holes through the top and bottom sleeve walls. For ease of insertion of the pins through the tendon, each pin can be formed with a sharpened tip portion 38 projecting from one pin end portion 28. A peripheral groove 40 can be formed between the sharpened tip portion 38 and the adjacent end portion 28 for ease in cutting away the tip portion after insertion of the pin so that the remaining pin end will be flush with the outer periphery of the sleeve.

Alternatively, the pin can be weakened sufficiently by the peripheral groove 40 that the tip portion can be broken off following insertion.

The modified pin 22' shown in FIG. 7 and FIG. 8 is substantially identical to the pin 22 shown in FIGS. 5 and 6, except that pin 22' is provided with a separate stainless steel sharpened tip 38' having a rear blind bore 42 for fitting on a corresponding cylindrical stud 43 molded integrally with the remainder of pin 22'. The stainless steel tip can be press fitted to or otherwise secured to the stud 43, such as by a suitable adhesive. In other respects, the pin of FIGS. 7 and 8 is identical to the pin previously described, including the peripheral groove 40 between the tip and the adjacent end portion 28.

Testing was conducted with a prototype splice sleeve having the approximate dimensions given above, but with larger diameter pin holes and pins (approximately 0.033 inch) arranged in a 2-3 configuration at each side of the sleeve. Flexor tendons were harvested from fresh-frozen cadaveric hands. A tendon having a cross-sectional area approximately the same as the area encompassed by the inner periphery of the prototype sleeve was selected and severed using a surgical scalpel. The severed tendon end portions were fitted in the splice sleeve and secured with five pins at each side. The splice sleeve was formed of a polyimide polymer, nonbioabsorbable but similar in physical properties to bioabsorbable polydioxanone. One free end of the spliced tendon was clamped to a stationary block. The remaining free end was clamped to a low friction slide which, in turn, was secured to a cable. The cable was suspended over a single pulley and different weights then were secured to the hanging cable end to apply different tensile loads to the spliced tendon.

The spliced tendon remained in place at a tensile load of 46.9 Newtons (4.78 kilograms of vertical load) for 66 seconds at which time the testing structure, not the splice, failed. The splice, with the tendon and pins in place, was removed from the testing structure and examined. No evidence of failure was seen. The cut tendon ends remained visibly opposed within the observation portals, with no evidence of separation or gapping at the repair site. In contrast, similar testing was performed using flexor tendons "repaired" by suturing. The suture repair site showed signs of visible gapping upon application of 16.7 Newtons to 21.6 Newtons (1.70 to 2.20 kilograms of vertical load). The sutured repair failed immediately when tensile load was increased to 24.5 Newtons (2.50 kilograms of vertical load).

After repeat testing, some splitting of the tendon fibers adjacent to the connection pins was seen at higher forces. Consequently, it is preferred that the number of pins be increased and that the pin diameter be decreased to about 0.023 inch to 0.025 inch for a more uniform application of force throughout the repair site. The surprisingly strong forces that can be withstood without substantial separation of the abutting severed ends indicates that the splice can be used for connective cords stressed at higher loads than those normally applied to flexor tendons.

In the embodiment shown in FIGS. 9 and 10, the modified sleeve 100 has a long integral hinge joint 102 along one side. The sleeve can be opened in clamshell fashion to the position shown in FIG. 9 for reception of the severed end portions of the cord. Thereafter the sleeve can be closed to the condition shown in FIG. 10. The top and bottom portions of the sleeve have aligned holes 24 for pins 22, 22' of the type previously described. Preferably, a central observation port 30 is provided in at least the top of the sleeve. At the side opposite the hinge joint 102, the sleeve has flanges 104 that abut when the sleeve is closed. The flanges can be stapled, clipped, sutured or otherwise secured together to maintain the sleeve in the closed position. Sleeve 100 has the same physical characteristics as the previously described embodiment. More than one longitudinally extending hinge joint can be used at the closed side of the sleeve.

Depending on the application, it may be desirable for the sleeve in accordance with the present invention to flex or bend for smooth excursion of the repaired cord. In the embodiment illustrated in FIG. 11, the modified sleeve 110 has an array of openings 112 designed to enhance flexing or bending of the sleeve, without altering its rigidity in a longitudinal direction or its ability to rigidly anchor the connection pins. Stated in another way, although the sleeve can bend or flex, preferably it will not change its longitudinal dimension substantially which could alter the abutting relationship of the severed ends of the cord C, and preferably the transverse cross-sectional shape is not altered substantially. It is most important that the sleeve be able to bend or flex in the direction of its minor axis, i.e., up and down as viewed in FIG. 11. The pattern of openings 112 can be selected to allow greater flexibility of the sleeve in that direction while minimizing longitudinal deflection. As for the previously described embodiments, the cord ends can be secured in the sleeve by pins 22 extending through aligned holes 24 in the top and bottom surfaces of the sleeve.

Figure 12:
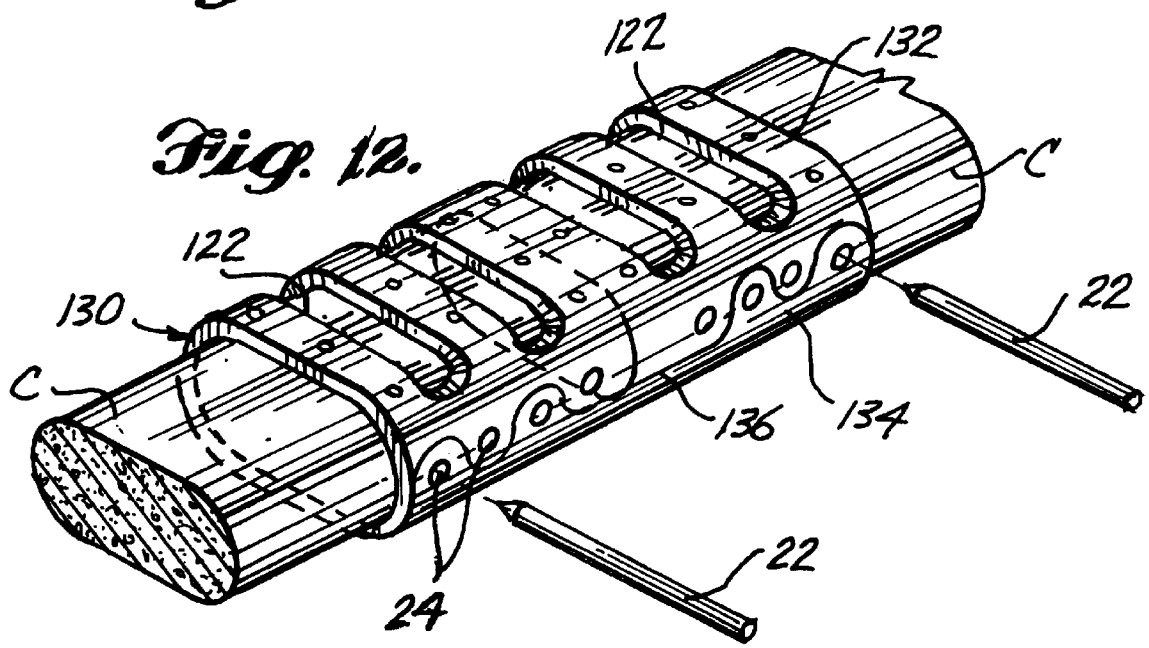
FIG. 12 is a top perspective of another alternative form of a splice in accordance with the present invention.
Figure 16:
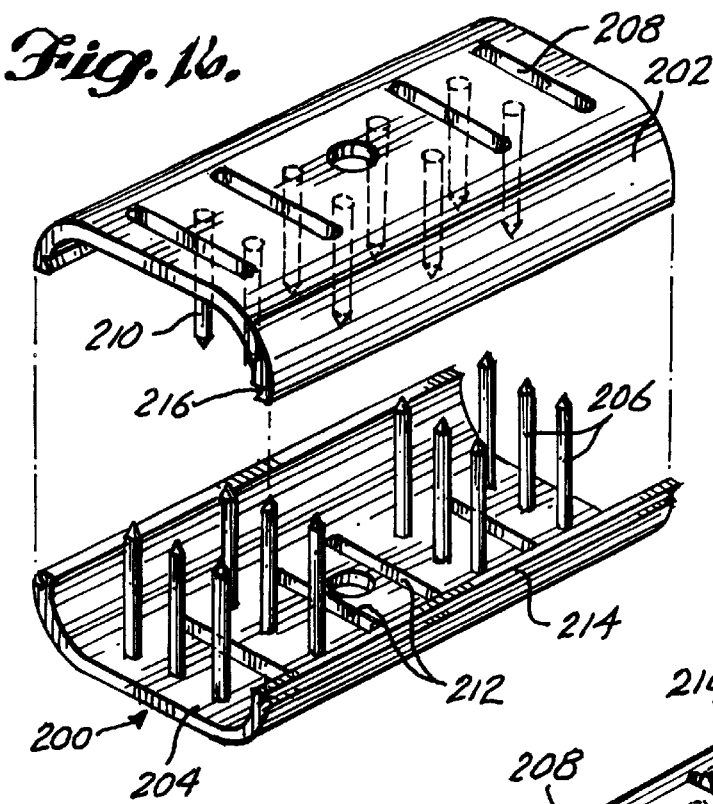
FIG. 16 is a top perspective of another embodiment of a splice in accordance with the present invention, with parts shown in exploded relationship.

The embodiment illustrated in FIGS. 12 and 13 uses a reinforcement member or sleeve 130 having transversely extending slots 122 in the top and bottom. However, sleeve 130 has separate top and bottom pieces 132 and 134, respectively. The top piece 132 and bottom piece 134 meet substantially contiguously at the sides along a scalloped border 136. The cord ends can be held within the sleeve by horizontal pins extending transversely between aligned holes 24 in the opposite sides of the sleeve, and/or by sutures. In other respects, the sleeve is the same as previously described.

A clamshell embodiment of the present invention is shown in FIGS. 14 and 15. Sleeve 160 has a bottom section 162 with an array of rigid pins 164 projecting vertically upward therefrom. Two side-by-side top sections 166 are provided, joined to the bottom section 162 by integral hinge joints 168. The two top or "lid" sections 166 are spaced apart at the center of the sleeve. With the lids open, as illustrated in FIG. 14, the cord end portions and sleeve are moved relative to each other for piercing the cord end portions and retaining them in position, with the cord ends abutting at approximately the center of the sleeve. Thereafter, the lids 166 can be closed. The lids have lock tabs 170 that fit over projections 172 along the adjacent edge of the bottom section of the sleeve. Pins 164 project through holes 176 in the top sections. When the lid sections have been closed, the projecting end portions of the pins can be cut flush with the exterior of the sleeve. Preferably, the pins are provided in transversely extending rows, with the pins of each row staggered relative to the pins of the most closely adjacent row, and with each pin spaced from the adjacent pins by an amount equal to at least the diameter of a pin.

Figure 18:
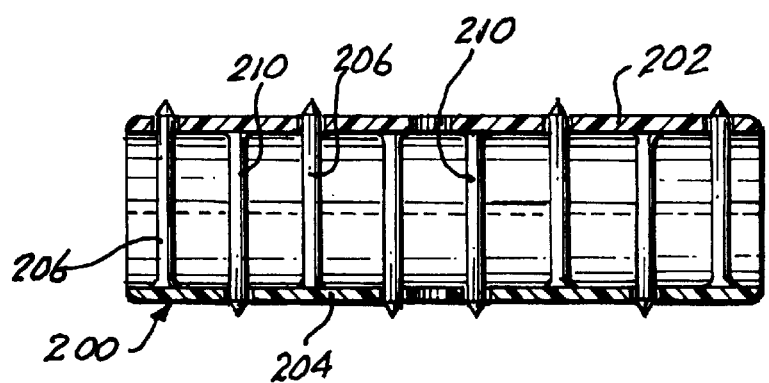
FIG. 18 is a longitudinal vertical section of the assembled splice of FIG. 17.
Figure 25:
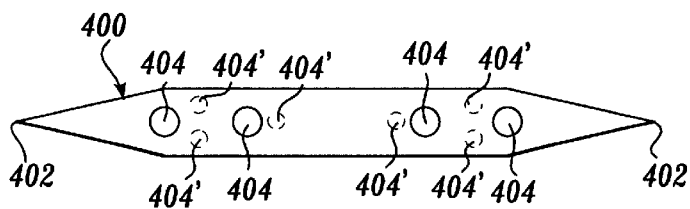
FIG. 25 is a top plan of an internal reinforcement member usable in a repair system in accordance with the present invention.

In the embodiment shown in FIGS. 16–19, the modified splice 200 in accordance with the present invention has separate top and bottom sections 202 and 204, respectively. The bottom section has straight rigid pins 206 projecting upward therefrom in alignment with transverse slots 208 through the top section. Similarly, the top section 202 has pins 210 projecting downward in alignment with transverse slots 212 of the bottom section. When the top and bottom sections are brought together, the free end portions of the pins fit in the slots of the other section, as best seen in FIG. 18. This helps to assure that the pins are held firmly in a vertical position without deflecting. The projecting sharpened tips of the pins can be cut flush with the periphery of the sleeve.

Figure 19:
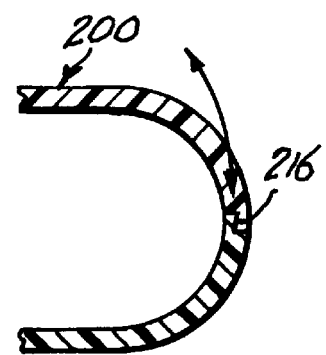
FIG. 19 is a fragmentary transverse vertical section of the assembled splice of FIG. 17.
Figure 17:
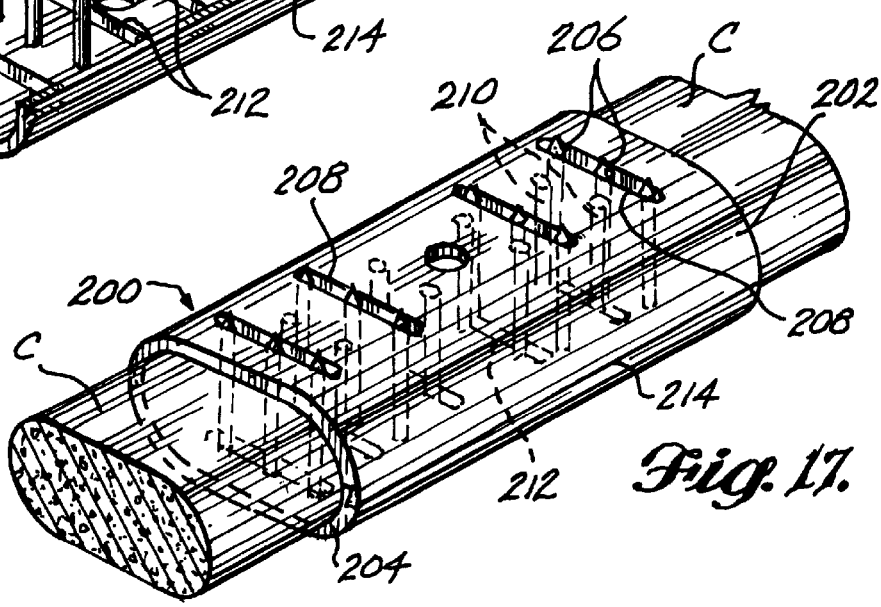
FIG. 17 is a top perspective corresponding to FIG. 16 but with parts assembled.

In addition, the bottom section has an undercut shoulder 214 extending lengthwise along its upper edge portions, to mate with a corresponding lip 216 of the top section. The lip 216 interfits with the undercut shoulder portion as best seen in FIG. 19 for holding the top and bottom sections together after the severed cord ends have been secured in position.

The embodiment illustrated in FIG. 20 has separate collars 242' secured to the severed cord end portions, respectively, such as by suturing or rigid pins extending through opposing faces. One collar 242' (the collar at the top in FIG. 20) has transversely spaced bosses 252 at the top and bottom. Flexible line or rail members 254 extend from bosses 252, and through aligned holes in the bosses 256 of the other collar. After the severed end portions of the cord are affixed in their respective collars, the collars are brought together and held in position by tying off the projecting free end portions of the rails or by otherwise fixing the rails in the bosses 256 through which they otherwise would slide. Preferably the bosses 252,256 would have a lower profile and be a smooth transition from the periphery of the associated collar.

The embodiment of the present invention illustrated in FIGS. 21 and 22 uses a composite sleeve 270 having two separate end collars 272 and 274 spaced apart by a center collar 276. The adjacent ends of adjacent collars can have matching undulating edges 278 including, for example, central humps or nose portions 280 on collars 272 and 276 received in central depressions or valleys 282 of collars 276 and 274, respectively. The separate collars are connected together by links 284 which permit limited resilient flexing of the collars relative to each other, particularly in the direction of the minor axis of the composite sleeve. The inner periphery of the sleeve preferably is smooth with no internal projections which would hinder fitting of the collars on the severed end portions of a damaged connective cord.

Links 284 can be formed integrally with connection pins 286 that project perpendicularly downward therefrom. Holes 288 are provided in the tops and bottoms of adjacent collars, with recesses 290 at the top sized to receive the links. When the pins are inserted downward through a cord, the tops of the links lie flush with the remainder of the periphery of the composite sleeve 270. The bottom ends of the pins can be sharpened and include necks 292 of reduced diameter for snapping into the holes 288 in the bottom surfaces of the collars. Any projecting portions of the sharpened tips at the bottom can be cut off. At least the upper portion of the middle collar 276 can have observation ports 297 for viewing the abutting end portions of the damaged cord to assure that they abut prior to insertion of the pins.

With reference to FIG. 22, the links 284 bridge between adjacent collars, such as collars 274 and 276, and can be dimensioned to space the collars apart slightly, so as not to inhibit the flexing movement of one collar relative to another. In addition, the bridging portions of the links can have weakening grooves 294 which assist in permitting the flexing movement, preferably without introducing a tendency of the links to expand or contract lengthwise. For example, it still is preferred that the length of the composite sleeve 270 not increase or decrease substantially due to forces applied to the repaired cord. In addition, limited sideways flexing of the sleeve (in the direction of the major cross-sectional axis) can be permitted by tapering the depressions 290.

The embodiment illustrated in FIGS. 23 and 24, similar to the embodiment shown in FIGS. 21 and 22, uses a multi-part composite sleeve 300 including end collars 302 and 304 spaced apart by a middle collar 306. As for the embodiment of FIG. 21 and FIG. 22, the collars have identical cross sections and are aligned lengthwise of the centerline of the sleeve. Separate pins can be provided for extending through registered holes in the tops and bottoms for securing the collars to the damaged cord to be repaired. In the embodiment illustrated in FIGS. 23 and 24, three rigid pins 308 are provided for each of the two end collars 302 and 304, joined at the top by flush bridging portions 310. The middle section has two pairs of pins 312, each pair forming a transversely extending row with its pins staggered relative to the pins of the end collars. The pins of each pair can be connected by a flush bridging portion 314. The pairs of pins 312 are arranged at opposite sides of the center of the sleeve such that each pair penetrates a different severed end portion of the damaged cord.

To allow flexing of the sleeve in the direction of its minor axis, connecting links 316 are provided at each side. One end of each link is pivotally connected to an end collar, and the other end of each link 316 is pivoted to the center collar 306. As seen in FIG. 24, the links are received in tapered recesses 318 which allow limited swinging of the links relative to the collars to which they are connected. The pivotal connection can be achieved by inward projecting buttons of the links being snap fitted in corresponding holes of the collars.

Figure 26:
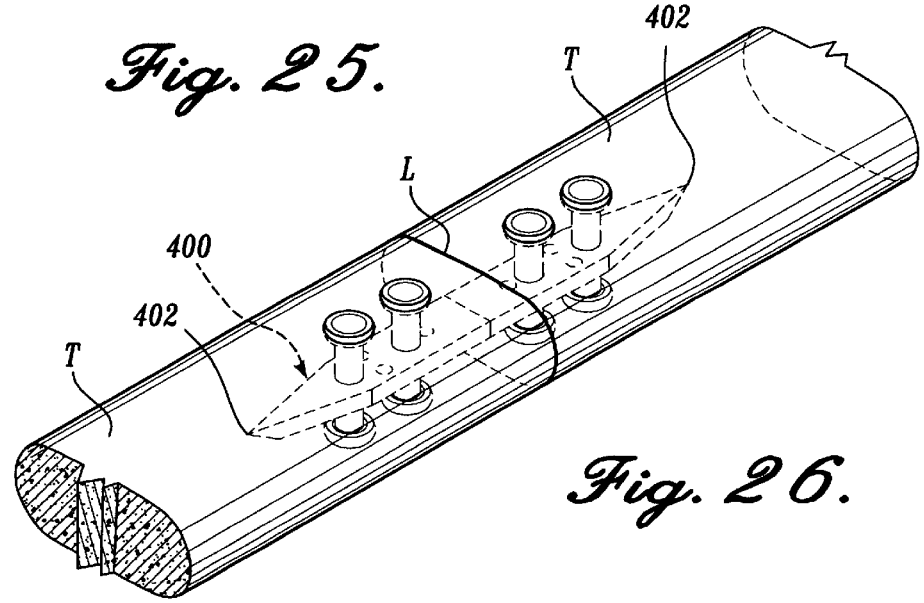
FIG. 26 is a top perspective of a severed fibrous cord repaired in accordance with the present invention using the reinforcement member of FIG. 25.

FIGS. 25–28 show another type of rigid or semi-rigid reinforcement member 400 used to repair soft tissue T, as illustrated in FIG. 26, where a tendon is severed at location L. The reinforcement member 400 is a flat band inserted lengthwise into first one and then the other of the severed cord (tendon) ends. The band preferably has sharpened ends 402. In the embodiment illustrated in FIGS. 25–28, the band is of substantially uniform width and thickness except for the sharpened ends, and has a series of through holes 404 aligned lengthwise of the band. Alternatively, smaller diameter holes 404' can be provided, including two holes in a transversely extending row, one at each side of the longitudinal centerline of the reinforcement member or band 400, and a third hole spaced longitudinally of the band from the first two holes and located approximately on the centerline.

Figure 27:
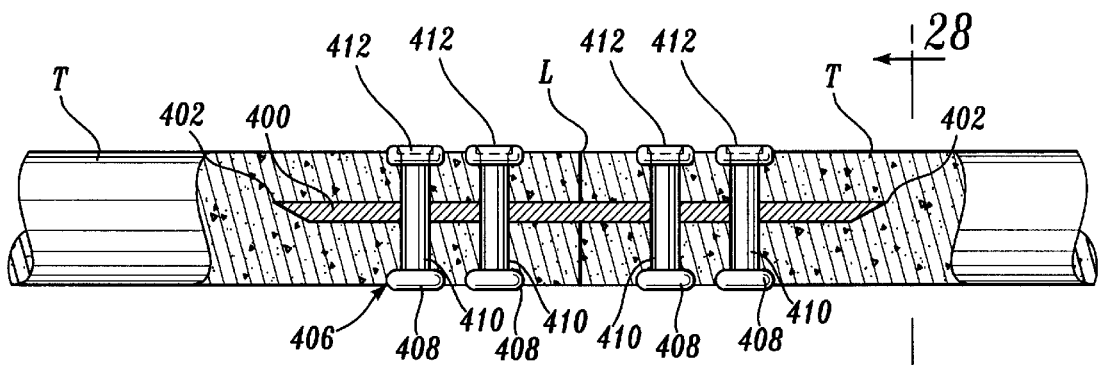
FIG. 27 is a side elevation of the repaired cord of FIG. 26, with parts broken away.
Figure 28:
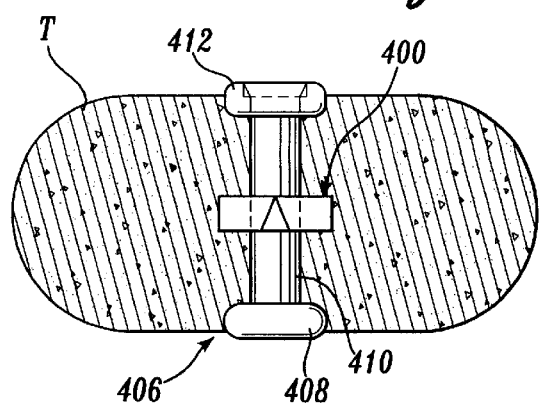
FIG. 28 is a vertical transverse section along line 28—28 of FIG. 27.
Figure 29:
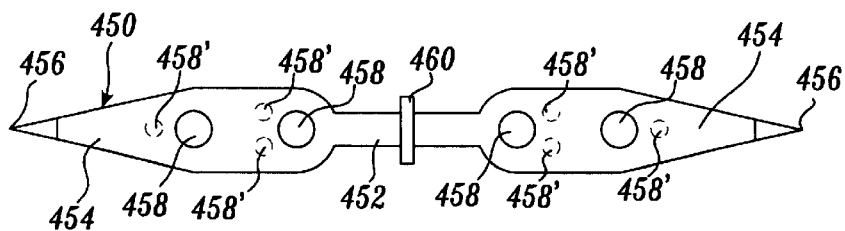
FIG. 29 is a top plan of an alternative reinforcement member usable in a repair system in accordance with the present invention.
Figure 30:
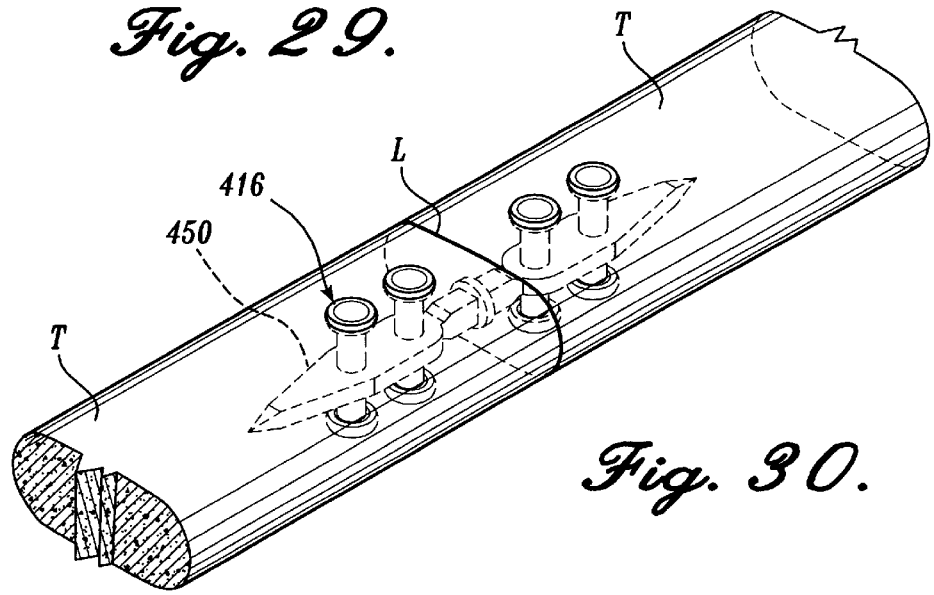
FIG. 30 is a top perspective of a severed cord repaired using the reinforcement member of FIG. 29.

The reinforcement member or band 400 can be secured to the tissue T by transversely extending pin assemblies 406, the details of which are seen in FIGS. 27 and 28. Each pin assembly 406 includes a first pin component having an enlarged head 408 and a shank 410 of a size for fitting closely in the holes 404 or 404'. The pins are firmly enclosed in and positioned by the snug engagement in the holes of the reinforcing member so as not to deflect or bend longitudinally of the cord when tension is applied. A second component includes a ring or collar 412 adapted to be fitted over the end of the shank 410 opposite the enlarged head 408. Collar 412 is of approximately the same diameter as the enlarged head 408, i.e., substantially greater than the reduced diameter shank 410 of the pin assembly. The smaller end of the shank adjacent to the collar can be crimped or otherwise upset to retain the collar in position.

As seen in FIGS. 27 and 28, the enlarged heads 408 and collars 412 of the pin assemblies can be sized and crimped for compressing the tissue being repaired. In the case of a tendon, the enlarged heads of the pin assemblies are intimately engaged with the epitenon. This is believed to be important if the repaired tendon is to withstand substantial tensional forces while healing. For example, mechanical strength tests were performed on sheep tendon with and without the epitenon, by piercing the tendon diametrally with a single 0.020 inch diameter steel pin and applying force to the pin axially of the tendon. The ultimate pullout strength of the pin was decreased by about 50% when the epitenon was removed—about 30 Newtons with the epitenon intact and about 15 Newtons with the epitenon removed. To further increase the pullout force, pins corresponding to the smaller diameter, staggered holes 404' (FIG. 25) can be used, which has the effect of spreading the tensional forces more uniformly throughout the cross-section of the tendon.

Figure 31:
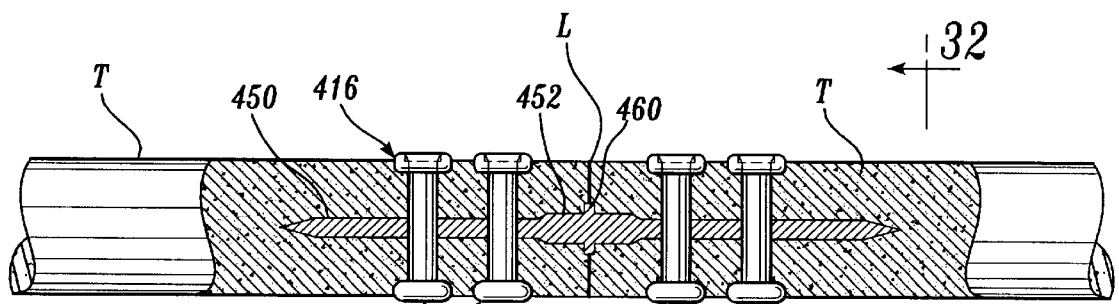
FIG. 31 is a side elevation of the repaired cord of FIG. 30, with parts broken away.
Figure 32:
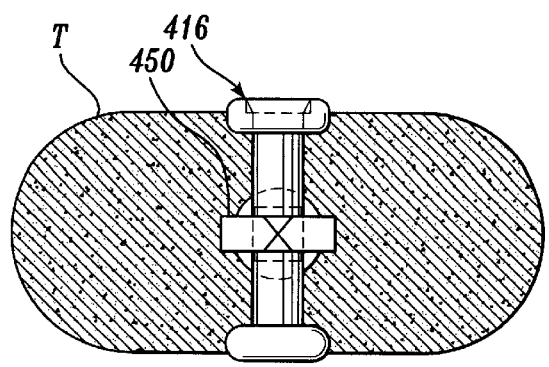
FIG. 32 is a transverse vertical section along line 32—32 of FIG. 31.

In the embodiment of FIGS. 29–32, an internal reinforcement member 450 has a narrow central portion 452 and wider opposite end portions 454 with sharpened ends 456. The wider end portions have holes 458 or 458' to receive the pin assemblies 416. The narrow central portion 452 of the device connecting the enlarged ends is thicker than the ends, as seen in FIG. 31, and such central portion has a short central disc projection 460. The thicker center and central disc are positioned adjacent to the severed ends of the tissue or cord T. The disc 460 and thicker central portion 452 help to maintain the ends in alignment by flexing to a lesser degree than the end portions 454, such as during normal excursion of the tendon following the repair.

Figure 33:
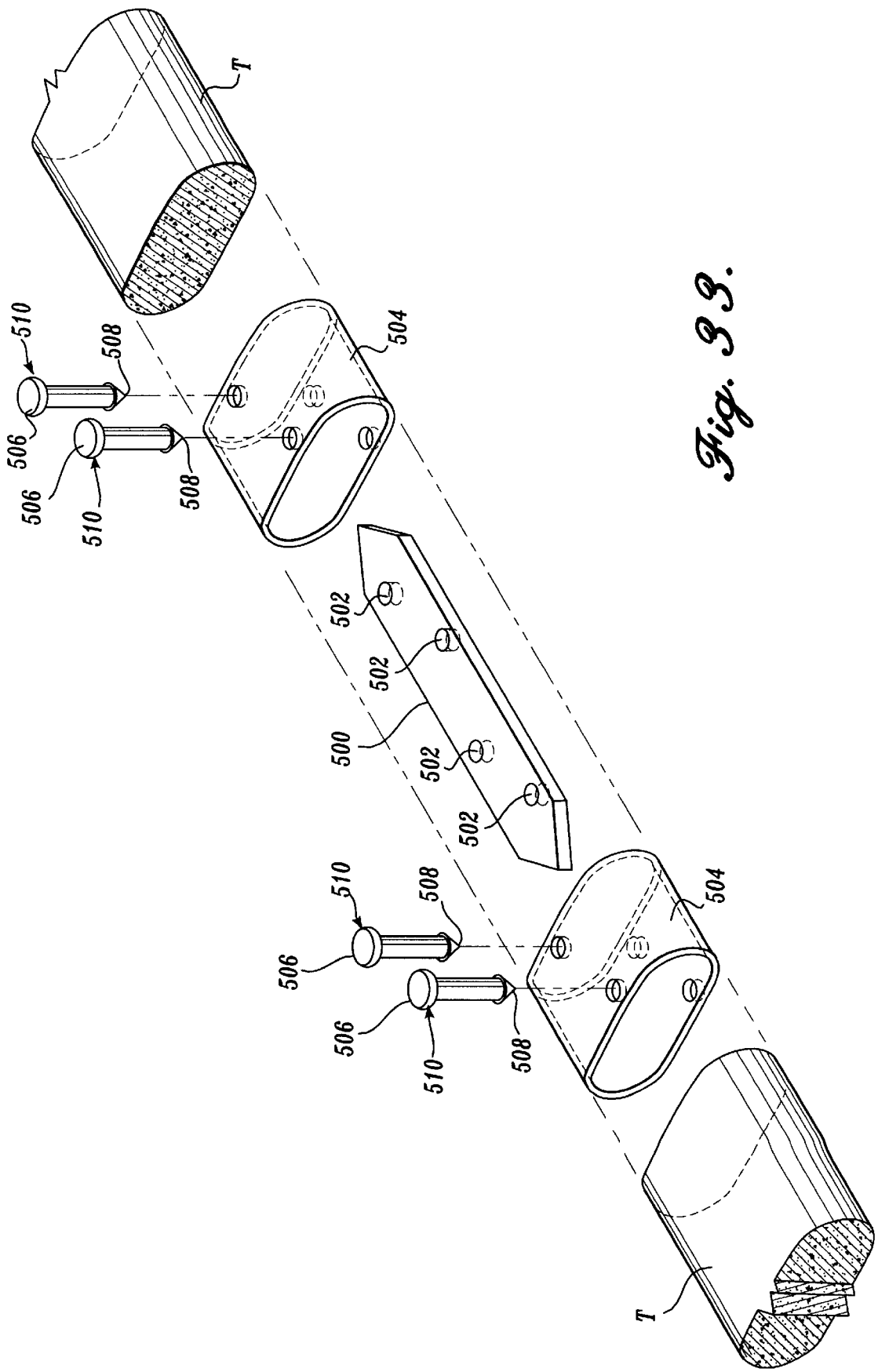
FIG. 33 is a top perspective of a severed cord repaired with another embodiment of a repair system in accordance with the present invention, with parts shown in exploded relationship.
Figure 34:
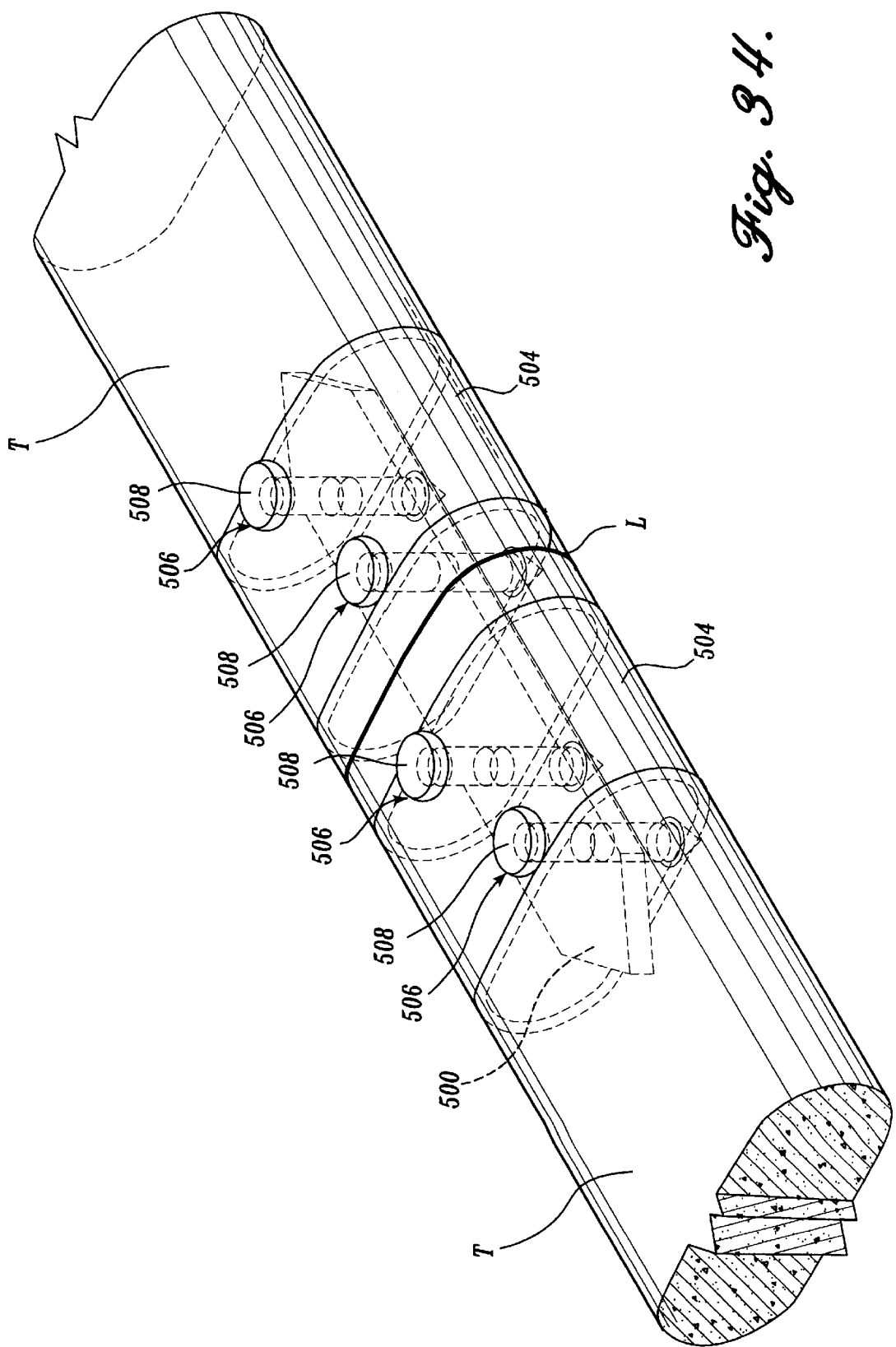
FIG. 34 is a top perspective corresponding to FIG. 33, but with parts assembled.

The embodiment shown in FIGS. 33 and 34 uses an internal reinforcement member 500 of the general type previously described, preferably with two holes 502 at each end of the device. The holes of each pair are offset relative to the longitudinal centerline. At each end, two thin (approximately 0.008 inch thick) flat band sleeves 504 wrap around the outside of the tendon and act to constrain it. Pins 506 having sharpened ends 508 and enlarged heads 510 pass through the sleeves 504, then through the holes 502, and finally through the opposite sides of the sleeves. The dimensions are exaggerated in FIGS. 33 and 34, preferably the pins would not have abruptly projecting ends, particularly in the case of tendon repair. Rather, the ends would be smoothly contoured into the sleeves, with the sleeves depressed into the epitenon so as not to unduly interfere with excursion of the tendon during healing. Tension applied to one cord end is transmitted generally from one sleeve and associated set of pins, through the reinforcement member, and through the other set of pins and associated sleeve to the opposite cord end.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A splice for repair of a severed connective cord normally tensioned in the body during joint movement, said splice comprising a reinforcing member of substantially rigid or semirigid material, said member being adapted for extending longitudinally between severed end portions of a connective cord with the severed end portions in abutting relationship, and means for securing the cord to the reinforcing member such that tension applied to the cord is transmitted through the reinforcing member and for maintaining the severed ends abutting as tension is applied to the cord by transmitting tensional force through the reinforcing member, the securing means including a plurality of pins anchored in the reinforcing member and extending at least part way through the connective cord for transmission of tensional force from the connective cord through the pins and the reinforcing member.

2. The splice defined in claim 1, in which the reinforcing member includes a hollow sleeve sized to closely receive the adjacent end portions of the severed cord.

3. The splice defined in claim 1, in which the reinforcing member is elongated and adapted for extending internally of the abutting severed cord end portions.

4. The splice defined in claim 3, in which the pins extend oppositely from the reinforcing member, transversely of the connective cord.

5. The splice defined in claim 3, in which the securing means includes at least one sleeve component adapted to encircle the cord, the pins being adapted to extend through the sleeve component and the reinforcing member.

6. The splice defined in claim 5, in which the pins have opposite ends adapted to be embedded in opposite sides of the sleeve compartment.

7. The splice defined in claim 1, in which the securing means includes a plurality of pins extending through each of the abutting end portions of the severed cord.

8. The splice defined in claim 7, in which the pins extending through each of the abutting end portions of the severed cord include pins which are offset from each other.

9. The splice defined in claim 7, in which the pins extending through each of the adjacent ends of the severed cord are arranged such that tension applied to the cord is transmitted substantially uniformly throughout the cross section of the cord.

10. The splice defined in claim 1, in which the pins are anchored in the reinforcement member so as not to flex or deflect in a direction longitudinally of the cord.

11. The splice defined in claim 1, in which the reinforcement member is adapted to flex transversely of the length of the cord without substantial change in the length of the reinforcement member while still maintaining the adjacent ends of the severed cord in abutting relationship.

12. The splice defined in claim 11, in which the reinforcement member is constructed so as to be less flexible in the area bridging between the abutting ends of the severed cord than at locations farther from the adjacent ends of the severed cord.

13. The splice defined in claim 1, in which the securing means includes a plurality of rigid pins arranged in rows with the pins of one row offset from the pins of an adjacent row.

14. The splice defined in claim 1, in which the pins are of a diameter no greater than about 0.025 inch.

15. The splice defined in claim 1, in which the pins have enlarged heads at their opposite end portions adapted to engage the epitenon of a severed tendon.

16. The splice defined in claim 15, in which the enlarged heads of the pins are adapted to compress into the epitenon.

17. The splice defined in claim 1, in which the pins have opposite ends adapted to be substantially flush with the outer periphery of the connective cord.

18. The splice defined in claim 1, in which the pins are provided in multiple pieces including an elongated shank having an enlarged collar adapted to interfit with the sharpened end.

19. The splice defined in claim 1, in which the reinforcing member is formed of bioabsorbable material.

20. The splice defined in claim 19, in which the splice is formed of bioabsorbable material selected to absorb into the body over a preselected period of time but at a rate no greater than the rate of healing of the cord such that at each stage of healing the combined strength of the splice and the healing cord is at least equal to the maximum force to which the cord is normally subjected.

21. The splice defined in claim 1, in which the reinforcing member has a plurality of preformed holes, the securing means including pins having shanks of predetermined cross-sectional shape and size for tightly fitting in the preformed holes of the reinforcing member.

22. The splice defined in claim 1, in which the reinforcing member includes a first component adapted to bridge between the adjacent ends of the severed connective cord, a second component adapted to overly the exterior of one of the adjacent ends of the severed cord, a third component adapted to overly the other of the adjacent ends of the severed connective cord, and a plurality of pins for connecting, respectively, the second and third components with the first component.

23. A splice for repair of a severed connective cord normally tensioned in the body during joint movement, said splice comprising a reinforcing member of substantially rigid or semirigid material, said member being adapted for extending longitudinally between severed end portions of a connective cord with the severed end portions in abutting relationship, and means for securing the cord to the reinforcing member such that tension applied to the cord is transmitted through the reinforcing member and for maintaining the severed ends abutting as tension is applied to the cord by transmitting tensional force through the reinforcing member, the splice being formed of bioabsorbable material selected to absorb into the body over a preselected period of time but at a rate no greater than the rate of healing of the cord such that at each stage of healing the combined strength of the splice and the healing cord is at least equal to the maximum force to which the cord is normally subjected.

* * * * *